United States Patent [19]

Jacobsen et al.

[11] 4,141,359
[45] Feb. 27, 1979

[54] EPIDERMAL IONTOPHORESIS DEVICE

[75] Inventors: Stephen C. Jacobsen; Robert L. Stephen; R. Todd Johnson; Richard Luntz; David Knutti, all of Salt Lake City, Utah

[73] Assignee: University of Utah, Salt Lake City, Utah

[21] Appl. No.: 714,942

[22] Filed: Aug. 16, 1976

[51] Int. Cl.² .............................................. A61N 1/30
[52] U.S. Cl. ................................ 128/172.1; 128/417; 128/419 R
[58] Field of Search ..................... 128/172.1, 404, 407, 128/408, 409, 417, 419 R, 303.13, 303.14, 303.17, 2.1 P

[56] References Cited

U.S. PATENT DOCUMENTS

| | | | |
|---|---|---|---|
| 3,289,671 | 12/1966 | Troutman et al. | 128/172.1 X |
| 3,683,923 | 8/1972 | Anderson | 128/303.14 |
| 3,918,459 | 11/1975 | Horn | 128/419 R |
| 3,933,157 | 1/1976 | Bjorwill | 128/303.14 |
| 3,991,755 | 11/1976 | Vernon et al. | 128/172.1 |

FOREIGN PATENT DOCUMENTS

| | | | |
|---|---|---|---|
| 1139927 | 11/1962 | Fed. Rep. of Germany | 128/303.13 |
| 2439587 | 2/1975 | Fed. Rep. of Germany | 128/2.1 P |

Primary Examiner—Lee S. Cohen
Attorney, Agent, or Firm—Criddle, Thorpe & Western

[57] ABSTRACT

An improved iontophoresis device for topical administration of ionic drugs or chemicals through epidermal tissue for anesthetizing or sterilizing local tissue or for applying various medicaments without mechanical penetration. An ionic form of drug is conducted through the epidermal tissue by means of direct current generated from a battery powered current source. Pulse-width modulated DC current is regulated by feedback circuitry which varies the pulse duration and adjusts and stabilizes the average current at a desired level. A high voltage capability together with feedback control enables maintenance of a constant current through the highly resistive epidermal tissue. To prevent excessive voltage buildup and the accompanying dangers of shock and burns, a comparator circuit monitors current flow and voltage across the electrodes and automatically triggers an SCR shutdown circuit when impedance readings are outside predetermined limits. The ionic drug is suspended in a conductive gel mixture which acts as the conducting medium in direct communication with the patient's skin. This gel is carried in a receptacle mounted on an electrode pad which uses a conducting foil surface to make electrical contact with the gel.

9 Claims, 8 Drawing Figures

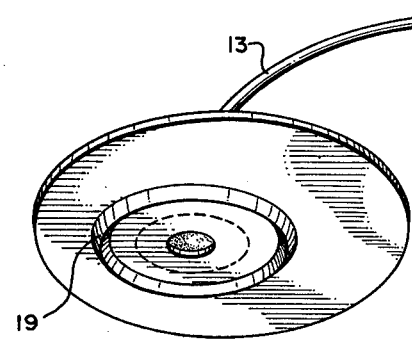
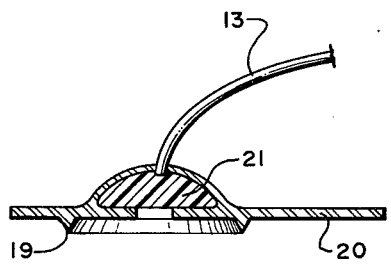
FIG. 5A           FIG. 5B
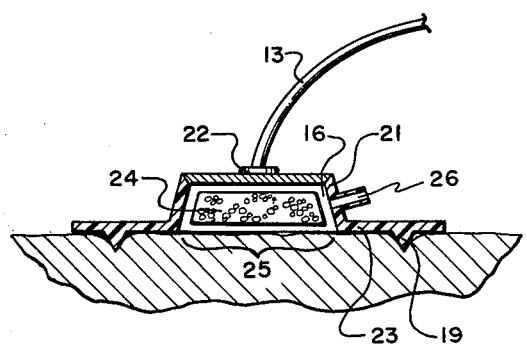
FIG. 6
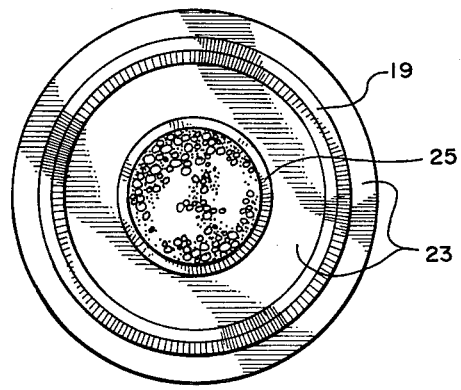
FIG. 7

EPIDERMAL IONTOPHORESIS DEVICE

BACKGROUND

Iontophoresis involves the application of an electric current to introduce ions of soluable salts into tissues of the body for the therapeutic purposes. This technique may be advantageously utilized in those cases where atopical application of such substances does not result in sufficient penetration into body tissue to accomplish satisfactory effects or where tissue penetration is otherwise undesirable. Application of the electric current causes migration of the ions into the tissue to greater depths, such migration being in proportion to the duration of current application and current density.

Iontophoresis devices have been developed for dental treatments in applying medications, anesthetizing agents, and desensitizing ions such as strontium and flouride. Essentially these devices consist of a battery, an applicator electrode carrying the ionic substance, and simple circuitry operable to provide a small current into the tissue to be treated. Typically, the circuit is closed by a grounding contact with the patients hand or other body surface. Generally, previous iontophoresis devices have operated as constant voltage devices, with varying current depending upon the impedance of the treated tissue.

Although a number of different embodiments of the above illustrated devices have been developed, utility has been limited to tissue such as that of the oral environment due to its relatively low impedance. Because of the more compatible electrical characteristics of this tissue, the iontophoresis device will effectively operate at low voltage. If the treatment area consists of epidermal tissue, however, the simple circuitry previously considered sufficient for oral applications will not be operative since the greater impedance within the conducting path requires a higher voltage to maintain effective current. Such higher voltage greatly increases the risk of shocks or burns to the patient and has discouraged a general application of iontophoresis treatments.

Inasmuch as the extent of ion migration is a function of the current flow, the rate of iontophoresis increases with a corresponding increase in current. Limitations as to the amount of current are based primarily on considerations of patient safety. If the current density becomes too high, the local resistance of the tissue results in burns or other electrical damage. Where tissue is burned, the resulting decrease in resistance increases current flow, compounding the danger of serious burns to the tissue.

A second limiting factor involves the discomfort associated with voltage applied to human tissue. Although current is the damaging force which causes burns and other physical disturbance, voltage is the primary cause of the alarming sensations of pain and shock. Voltages in excess of 40v will customarily become perceptable. The actual physical damage will depend upon the impedance of the tissue since the combined values of voltage and impedance define the amount of local current density. The high resistance of epidermal tissue frequently requires voltage capability which could easily exceed the 40v threshold and thereby result in pain to the patient. Since the primary object of this iontophoresis device is to provide a non-painful method of anesthetizing a patient, any patient discomfort due to high voltage will defeat this purpose.

Voltage can be minimized by maintaining the treated tissue at the lowest possible resistance. By utilizing appropriate techniques, epidermal impedance can be lowered to approximately 10K ohms to 40K ohms, depending upon the patient. Assuming a 15K ohms resistance across the electrodes and a 2 ma current, the required conduction voltage is 30v. Such a current level could be effectively used for iontophoresis on most patients without causing patient discomfort.

To minimize treatment time, an iontophoresis device should operate at the maximum current possible without causing burns or shocks, since lower current flow requires longer periods of application to reach the same degree of ion penetration. A constant voltage device is not suitable to provide a constant current to the variable higher impedance of epidermal tissue and the accompanying conductive gel. Although a constant current device will accomplish this purpose, additional circuitry for holding the maximum current through the electrodes is necessary to achieve optimal safe performance while at the same time protecting the patient from the aforementioned adverse effects of current regulation. Maintenance of the constant current results in proportional increases in voltage with an increase in impedance across the electrodes in accordance with Ohm's Law. Herein lies one of the major hazards of higher voltage, current regulated iontophoresis devices.

Assuming that the device is current regulated and operating at 3 ma in contact with the patient's skin, then if the device is suddenly removed a short distance from the skin, the increased impedance resulting from the additional air gap separating the electrodes develops an extreme surge in voltage as the circuitry attempts to maintain the 3 ma current. To suddenly return the electrode toward the skin might result in an electrical jolt due to the high voltage across the decreasing impedance. Such current surges result in shocks, burns and similar alarming and dangerous effects.

Consequently, the present application of iontophoresis treatment through epidermal tissue is generally limited to the pilocarpine test for cystic fibrosis in which pilocarpine is conducted into the patient to induce sweating. Unfortunately, the appreciable electric current required has resulted in the frequent occurrence of the aforementioned dangers. The incidence of burns is significant. Often, current flow reaches ranges capable of causing muscular spasms or ventricular fibrillation, particularly in small children.

The recurrence of such effects has been a major factor in discouraging the application of iontophoresis techniques to potential uses other than in the dental care area. The broad spectrum of utility of iontophoresis, however, suggests the need for a safe method which could provide painless local anesthesia and improved methods of asceptization for general medical use. Such a method could be applied prior to insertion of any needle, particularly large cannulae which are both painful and unnerving to patients. Small children and infants would be less fearful and more cooperative, thereby making the treatment procedures less difficult.

Patients on hemodialysis and hospital patients who often require regular insertion of large needles are frequently prepared by injection of a small amount of xylocaine to anesthetize the area prior to insertion. In addition to the pain and psychological effect of this initial injection, there are accompanying traumatizing effects to the skin. All of these adverse effects could be minimized with a safe method of epidermal iontophoresis.

As a corrolary to the aforementioned problems with injections, the removal of warts and treatment of boils, absesses and other infections which cause swelling and tensing of tissue create special difficulties. Desensitization of such sensitive tissue is frequently as painful as the nonanesthetical surgury and therefore defeats one of the primary purposes of the procedure. In addition to the pressure of the needle insertion, the high concentration of anesthetic at the opening of the cannula may result in a burning sensation until the drug difuses into surrounding tissue. Frequently the injected fluid forms a temporary pocket which deforms the tissue and increases pressure on the surrounding nerves. Such disfiguration resulting from fluid pockets is particularly troublesome in plastic surgery where the tissue must be in its natural condition to ensure proper reformation. Virtually any treatment involving conduction of medicament through the epidermis could be accomplished by iontophoresis techniques.

SUMMARY AND OBJECTIVES

This invention relates to an improved iontophoresis device for treatment of epidermal tissue and other tissue having high impedance, low mucous content or other adverse electrically nonconductive characteristics. Such treatments may be used for the purpose of anesthetizing a local region of tissue or for asceptically preparing such tissue for surgery. Other uses involving a variety of ionic materials are likewise envisioned within the potential applications of the subject invention.

A primary feature of this invention is the use of a pulse-width modulated DC-DC converter and appropriate feedback circuitry to provide effective and highly responsive regulation of a constant current across the electrodes. A safety cut-off circuit for protecting the patient from burns, shocks and similar adverse effects is provided to permit safe and simple operation. Inasmuch as most of the adverse effects of iontophoresis occur as a result of surges in voltage or current caused by variations of impedance across the electrodes, any suitable circuitry responsive to such changes may serve as the driving force to de-energize the current source. The present embodiment uses comparator circuitry to register impedance conditions outside a given set of parameters. Upon the occurrence of such conditions, a signal triggers a circuit which operates to shut down the current source. Various shut-down circuits are available in the art which could be utilized in connection with the de-energizing circuitry, including the triggered SCR-feedback circuit disclosed. Additional safety features of this invention comprise timing circuitry to enable an operator to pre-set the duration of current application and to provide for automatic turn off. A damping circuit is included to check sudden changes in current such as is experienced when the device is turned off after completion of the treatment. This precludes perception of adverse nervous reaction of spasm caused by nerve response to voltage variations.

The physical configuration of the device includes a wearable design which allows the operator to affix the electrodes to the patient in a manner which reduces possible accidental removal prior to completion of the treatment. The applicator electrode is used as the source of ionic material by encapsulating the material in gel form in a compartment of the electrode such that the material communicates directly with the skin upon application of the treatment. The relative spacial emplacement between the applicator electrode and grounding electrode is limited to preclude an arrangement resulting in current flow across the patient's heart.

The area of treatment may be marked by staining the surface of the treated tissue with a dye impregnated within the adhesive material on the contacting surface of the applicator electrode. An impression ridge may likewise be used for temporary indication of the treatment area. This automatic method of identifying the region of treatment reduces confusion during actual post-iontophoresic treatment and upon subsequent evaluations where knowledge of the exact location of the treated area is important.

It is therefore an object of the present invention to provide an iontophoresis device for treatment of epidermal and similar high impedance tissue.

It is a further object of this invention to incorporate an automatic safety shutdown capability for de-energizing the current source of an iontophoresis device.

A further object of the present invention involves the implementation of other safety and convenience devices for minimizing difficulties associated with iontophoresis treatment.

An additional object of this invention is to provide a method for identifying the previous location of electrode contacts such as those utilized in medical evaluations.

DESCRIPTION OF DRAWINGS

FIGS. 5A and 5B depicts two views of an electrode pad having an impression ridge for marking locations of application.

FIG. 6 is a cutaway view of an electrode having an injection tube for receiving a conductive gel.

FIG. 7 is a bottom view of the electrode illustrated in FIG. 6, showing the relative orientation of the impression ridge.

DETAILED DESCRIPTION OF THE INVENTION

Figure 1:
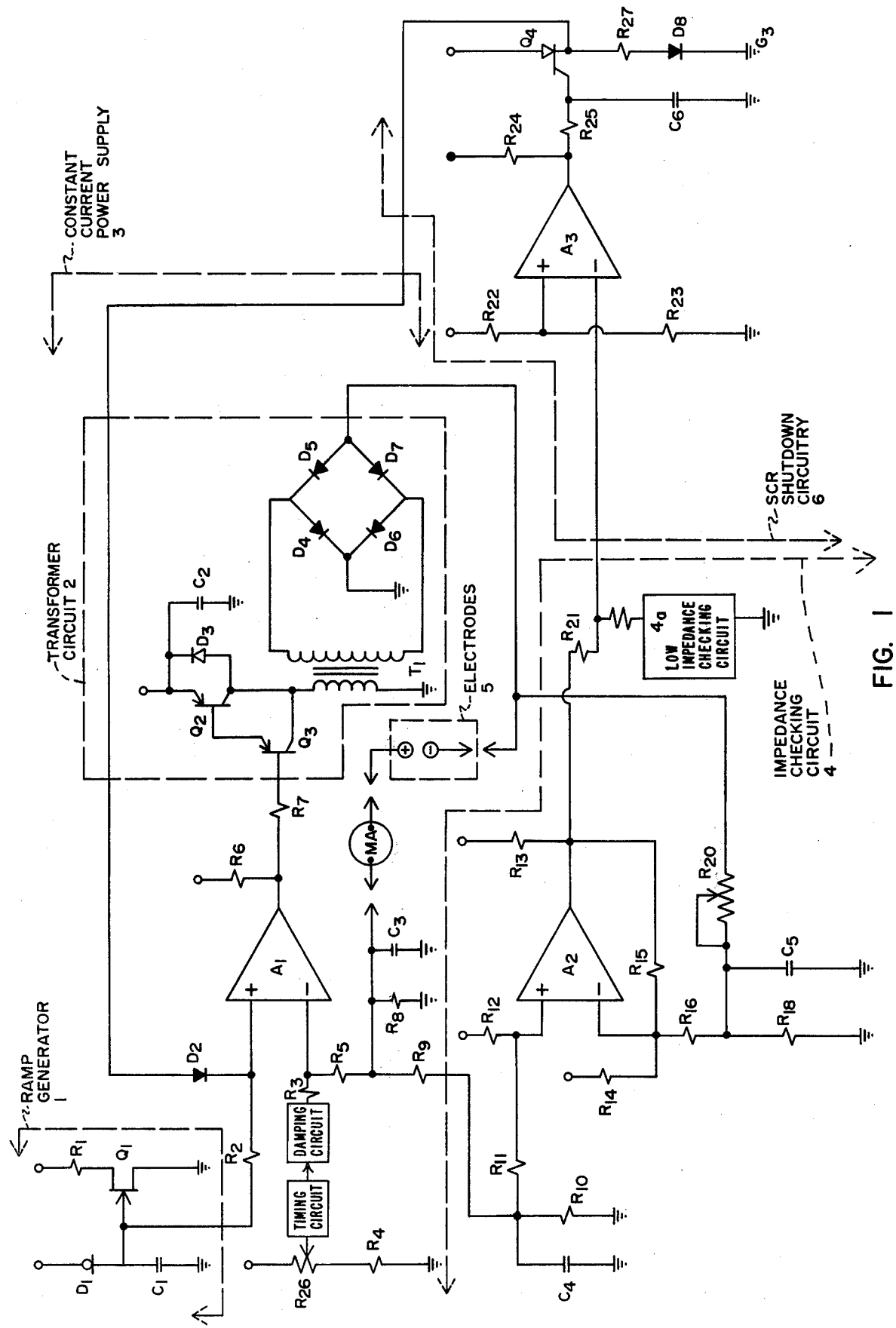
FIG. 1 is a schematic circuit diagram of a preferred embodiment of an iontophoresis device having the constant current power supply, impedance safety check shutdown circuitry.

This invention pertains to an iontophoresis device for general topical application of ionic drugs to high impedance low mucous tissue such as epidermis. Circuitry and physical configuration have been developed to ensure safe operation and to provide simplified procedures which require minimal training and technical ability. The essential elements of this device include (1) a pulse-width modulated DC-DC converter with a 9v–100v output range, having additional circuitry for rapid feedback response, (2) an impedance checking circuit for monitoring the impedance across the electrodes, (3) a shut-down circuit operable to de-energize the DC current source and (4) improved electrode configurations to ensure proper application, retention and marking of the treated tissue. Additional convenience circuits are discussed which facilitate simplified procedures of administration.

Although the principles of iontophoresis could possibly be adapted for alternating current, direct current is customarily utilized for conducting the ionic form of drug into the tissue to be treated. Inasmuch as the rate of flow of the ionic drug into the tissue is proportional to the current flow, the current should be regulated at the maximum constant level within the limits of safety and comfort in order to minimize treatment time. In view of variable impedance of the skin for each patient, the current source must have the capability of operating over a wide range of resistances, including the common epidermal range from 10K ohms to 50K ohms. Many of the hazards previously experienced by iontophoresis treatments have resulted by reason of this wide range of impedance.

Effective iontophoresis treatment generally requires a current in the range of 1 to 10 ma/in$^2$. The exact current density required will depend upon the thickness of the epidermis and the sensitivity of the patient to the applied voltage. At a given current, applied voltage is a function of resistance. Under certain conditions tissue resistance can be as high as 300K, such as where surface contact between the electrode and tissue is poor and where the tissue is dry and clean. By using an ionic gel as the conducting medium, the irregular surface of the epidermis can be fully contacted, thereby increasing the area of exposure and maximizing electrical contact with the tissue. The resultant decrease in impedance to a more favorable range of 10K to 50K reduces the voltage requirement and improves the realization of a safe and painless iontophoresis treatment. A decrease of resistance, for example, from 100K ohms to 20K ohms with 2 ma current results in a corresponding decrease in required voltage from 200v to 40v. Generally, any voltage above 100v would be prohibitive due to associated pain. Patient sensitivity becomes a factor at even lower voltages of approximately 40v. It will therefore be noted that the use of a conductive gel is imperative for safe and painless iontophoresis of epidermal tissue.

This same conductive gel may be utilized as the solvent for a solution of the ionic drug to be administered. The relative percentage of drug determines the rate of iontophoresis and consequently, the duration of treatment time required. Economic considerations of administration time versus material costs become the dominant factor in establishing the percent solution desired. For example, solutions as low as 2% can be successfully utilized, but they require a treatment time in excess of five minutes. Any chemically suitable ionic gel such as a salt solution can be effective as the solvent and will maintain the low voltage requirement to effect iontophoresis.

Previous devices have attempted to supply the voltage requirements in iontophoresis by voltage multiplier circuits, commonly incorporating a bank of capacitors. The present invention has avoided the use of capacitors as a storage source due to the fact that such capacitor banks can discharge their energy after termination of the treatment, causing unexpected shocks or burns. Instead of the standard DC source with a voltage multiplier, the present invention utilizes a pulse-width modulated DC-DC Converter in combination with a step-up transformer.

One embodiment of such a pulsed DC-DC Converter is disclosed in FIG. 1 and includes a ramp generator 1 which operates in combination with a comparator $A_1$ to switch on the conducting circuit through the primary coil of the transformer circuit 2 for an appropriate duration of time, causing a periodic rise and fall of current flow. These current variations are inductively coupled and amplified through the secondary coil, generating periodic surges of direct current across the electrodes 5.

The desired current level is maintained by means of a feedback circuit through R5 to the negative input of comparator $A_1$. Variations in current across the electrodes due to changes in impedance result in an error voltage which operates to adjust the duration of the pulse and thereby increase or decrease the average amount of current flowing through the transformer circuit. A current meter is shown in FIG. 1 and operates to permit manual adjustment of the current to an appropriate level for effective iontophoresis treatment.

In view of the ability of the iontophoresis device herein disclosed to maintain a constant current across the electrodes, an impedance checking circuit 4 has been incorporated to monitor the resistance as seen across the electrodes 5. This circuit operates as the primary safety check against shocking, burning and other adverse effects of high voltage or excess current. Such effects occur where impedance is high in the case of high voltage or where impedance is low in the case of excess current as experienced when tissue has been burned. Both contingencies should be checked to avoid serious physical damage.

It should be noted that inasmuch as the present iontophoresis device attempts to maintain a constant current, any rapid increase in impedance across the electrodes will generate a corresponding increase in voltage produced by the power supply. As seen by the electrodes 5 the impedance can change for a number of reasons. For example, if the electrodes are removed spacially from the contacted tissue, the resultant air gap is seen as a sudden increase in resistance. In response to such increase, the circuitry operates to increase the voltage in an attempt to develop the constant current previously maintained when the electrodes were in contact with the skin. If the electrodes are then brought in closer spacial relation to the tissue, the rapid decrease in impedance across the electrodes may result in a surge of current jolting or arcing due to the high voltage previously developed upon removal of the electrodes. This result has been previously experienced in iontophoresis treatments and has in the past discouraged the use of iontophoresis in general medical application.

Additionally, a sudden increase in iontophoresis current should be detected since this may indicate an abnormal drop in tissue impedance. Any such decrease in impedance will have the effect of increasing current flow through the tissue. Since current flow is the damaging force within the iontophoresis system, such changes should be continuously monitored in order to avoid the possibility of injury. This is particularly important in view of the fact that tissue impedance is lowered upon burning.

The function, therefore, of the impedance checking circuit is to provide monitoring within the circuitry to compare the impedance across the electrodes with predetermined limits which mark the bounds of safe operation. Such bounds are defined by an upper limit representing a high impedance which could lead to dangerous shocks upon a suddenly increased impedance, and a lower limit for detecting sudden increases in current due to abnormally low tissue impedance. Any circuit capable of comparing the voltage or resistance as seen by the electrodes with a set voltage or resistance can operate to trigger a signal for shutting down the current source. From the relationship defined by Ohm's Law, $$R = (E/1)$$

it will be noted that a multiplier or divider circuit could be utilized to identify the value of the resistance at any given time. This value could then be compared against predetermined parameters to determine if the impedance was within the safety limits previously indicated. Upon a variation outside these predetermined bounds, a shutdown signal would de-energize the current source.

Since a typical multiplier or divider circuit is quite complex, the present embodiment utilizes a comparator circuit which operates to monitor the combined respective values of voltage and current across the electrodes and compare this result with predetermined limits. The operation of this comparator is illustrated by the following graphic depiction of Ohm's Law.

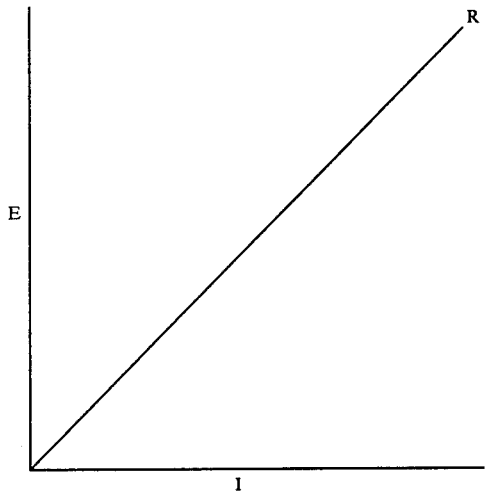

Referring to FIG. 1, comparator $A_2$ monitors the voltage level E at one input (positive) and the current level I at the other input (negative). Since the slope of E/I is equal to the resistance R, the input values can be compared against the appropriate values which should lie on line R. The slope of line R is preset by means of a variable resistor R-20. When E exceeds the predetermined value for a given I in accordance with the equation $E - IR = 0$, the comparator signals a second circuit to shut down the current source. In the clinical example previously mentioned in which the iontophoresis device was removed from contact with the skin resulting in a sudden surge of voltage to maintain the constant current, the impedance checking circuit would see a voltage substantially above line R. The current source would be de-energized and upon subsequent skin contact with the electrode no shock would be experienced.

A second comparator circuit 4a may be included within the impedance checking circuit to monitor excessive current across the electrode. Such a comparator combination is useful in view of the apparent decrease of resistance which occurs when tissue is burned. Being responsive to abnormal increases in current such as those due to burned tissue, such a circuit could signal the same shutdown circuitry to de-energize the current source and therefore operate as a fail safe device if for some reason the danger was not previously detected. By using a combination of comparators, the upper and lower operating limits for the iontophoresis device may be fixed between the preset impedance levels $R_1$ and $R_2$ as follows.

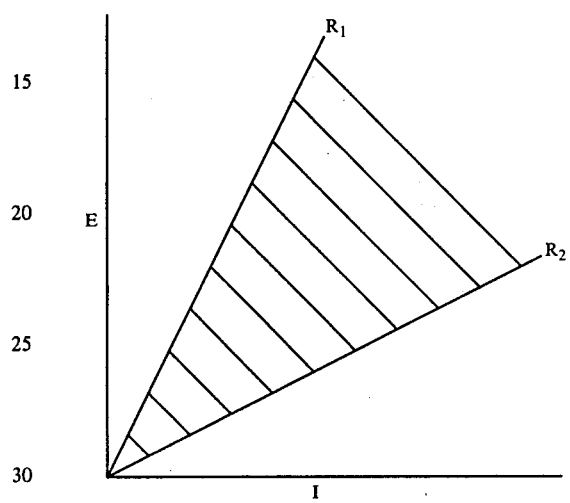

To simplify procedures so that non-technical personnel may apply the iontophoresis treatment, the present invention utilizes a final-state shutdown circuit. Such a circuit requires the operator to reset the various switches and begin the process from step one. This eliminates the possibility of placing an operating device in contact with the patient's skin and thereby experiencing an excessive current flow or arcing due to the sudden drop in resistance as the electrodes come in close proximity to the tissue. The impedance limits set for the impedance checking circuit can be adjusted such that the current source would be inoperative unless the electrodes were in direct communication with the tissue. Upon removal of an electrode, either intentionally or inadvertently, the circuit automatically shuts down and requires reapplication of the electrode to the tissue prior to resetting of the controls and recommencement of treatment procedures.

Although numerous shutdown circuits are available, the present device utilizes SCR-comparator combination 6 to de-energize the current source. Upon receiving an appropriate signal from the impedance checking circuit, comparator $A_3$ sets up an appropriate voltage to trigger the SCR, thereby turning off the conducting circuit in the transformer circuit. The SCR continues to conduct until the device is manually reset, at which point the operator may then commence the treatment procedures from the initial step. With the inclusion of the impedance checking circuit 4 and the shutdown circuit 6, the possibility of burns, shocks and other dangerous effects of excessive current and voltage are substantially reduced and the device can be safely operated by personnel having minimal technical ability.

It is suggested that additional convenience devices be incorporated to assist the operator by simplifying operation techniques. One such device is a timing circuit which is utilized to preset the duration of the treatment and automatically turn off the device upon completion. A second safety circuit is a damping circuit operable to preclude sudden changes in current such as may be experienced when the device is first turned on or later turned off. This circuit is useful since cutaneous sensors seem to be particularly sensitive to sudden variations in current flow. By limiting the incremental increases of current, the discomfort previously experienced is minimized. In an anesthetization treatment, the regulation has the additional benefit of permitting gradual desensitization of the skin as the degree of current flow increases, further eliminating any discomforts associated with current and/or voltage sensing.

Referring to FIG. 6, the present invention utilizes a compliant, plastic form of electrode pad 23 having an adhesive face for retaining the pad on the tissue to be treated. Alternatively, a strap may be used to retain the pad in contact with the tissue where adhesive contact is not suitable. The pad can be positioned over a variety of anatomical contours without tensing of tissue or awkward implacement. The compliant form of pad precludes localization of current flow that occurs at points where tissue has been stretched. Such localized current can present an increased risk of burns and should therefore be avoided.

The receptacle 16 for containing a suitable quantity of gel is mounted on the electrode pad and aligned with an opening 25 in the pad which permits direct communication of the conducting gel with the tissue. A sponge pad 24 may be enclosed within the gel receptacle which, upon saturation with the conductive gel, operates to maintain good fluid contact within the conduction path. Uniform electrical contact across the surface of treated tissue is maintained by utilizing a metal foil 21 in direct communication with the conducting gel to provide the current source for effecting the iontophoresis of the drug. A connecting wire 13 is attached from the current source to the electrode by means of a quick-release clip 22 mounted on the back surface of either the gel receptacle or metal foil. A primary advantage of this configuration, in addition to the safety features provided hereby, is the convenience of disposability after each treatment.

For commercial convenience, the electrode may be packaged in ready-to-use form, with the appropriate ionic gel prepackaged within the gel receptacle. The adhesive surface 23 would be exposed upon the removal of a protective covering from the electrode pad which would also operate to contain the ionic gel in a closed and sterile receptacle 16. Otherwise, the electrode pads could be stored in dry form, with the ionic gel being added immediately prior to application from a separate source.

When used in the dry form, the receptacle can be modified with a small inlet tube 26 for receiving the conduction-gel/ionic-drug solution for indefinite storage. When the electrode has been affixed to the patient immediately prior to treatment, the dispensing tube is inserted in the inlet tube of the receptacle. The tube contents are discharged into the receptacle, filling the vacancies and saturating the sponge pad 24. To simplify procedures, the ionic gel may be contained in a closed bad, the mouth of which is sealed to the electrode receptacle. The mouth of the bag has a weak seal which when broken, permits free flow directly into the receptacle. This configuration avoids the current problems associated with the drying out of the prepackaged conductive gel.

A variety of electrode configurations can be utilized to meet the requirements of safety and convenience. A safety factor which must be considered with each application is the avoidance of current conduction across the heart with the concurrent risks of fibrillation or muscle spasms. Such dangers can be avoided by limiting the lengths of the connecting wires to the electrodes such that restricted spacial separation of electrodes precludes an adverse circuit path.

As an illustration of several embodiments of the complete iontophoresis device, the following examples are cited:

EXAMPLE I

Figure 2:
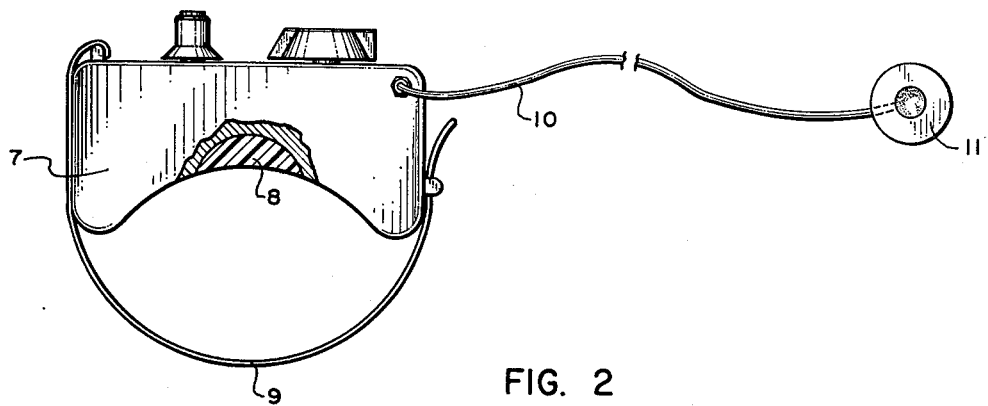
FIG. 2 is a longitudinal view of the container for the circuitry, the case operating as the grounding electrode and being in a contoured form for improved contact with curved body surfaces such as an arm or leg. An application electrode is electrically connected to the enclosed circuitry.

As illustrated in FIG. 2, the ground electrode can be a contoured casing 7 which also contains the required circuitry suggested in FIG. 1, having a suitable gel receptacle 8 on the contoured tissue contacting surface. This grounding electrode may be useful where treatments are intended for the extremities and may be mounted by elastic bands or straps 9 to the arm or leg of the patient such that the current is conducted away from the torso of the patient. A single wire 10 may be utilized to conduct the current to an applicator electrode 11 which could be of the disposable design. This conducting wire 10 should be sufficiently short to preclude a conduction path across the heart.

EXAMPLE II

Figure 3:
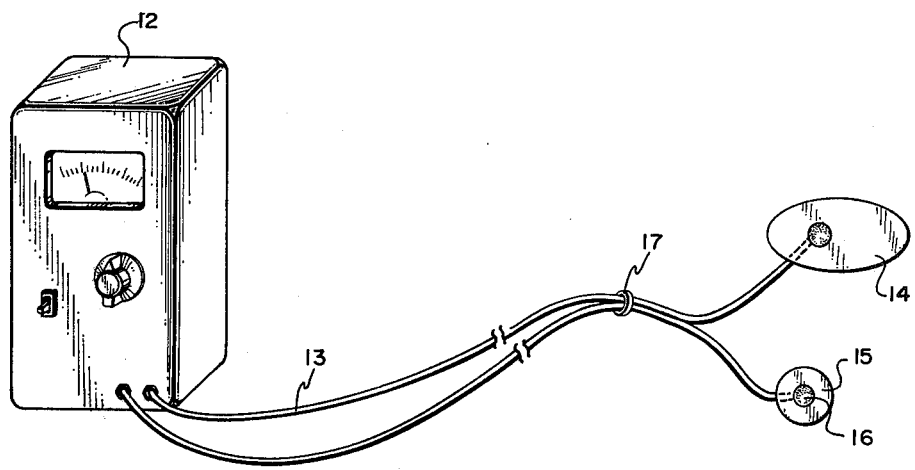
FIG. 3 shows an alternate configuration having electrodes separate from the circuitry housing.

FIG. 3 depicts how the electrical circuitry may likewise be contained in a separate housing 12 which may be clipped to the belt or otherwise retained on the patient. Electrical connection with the electrodes is accomplished by dual connecting wires 13 for separate applicator 14 and ground 15 electrodes respectively. In all cases, the grounding electrode pad should contain a receptacle 16 for a conducting gel to ensure appropriate electrical contact with the skin. A salt water gel is commercially available and would be suitable for iontophoresis treatment. The grounding electrode would be of similar construction of the applicator electrode. To provide adaptability for various contoured portions of the body, the applicator electrode could be constructed in such a manner that the operator could trim the pad to a suitable configuration for implacement around the nose, ears or similar anatomical protrusions. The conduction path could be limited by using a restricting device 17 to preclude an unsafe spacial separation between the electrodes.

EXAMPLE III

Figure 4:
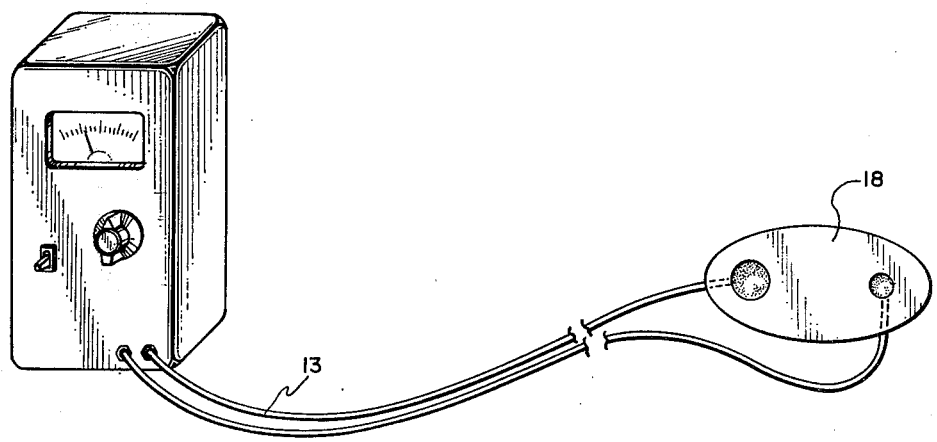
FIG. 4 illustrates the use of a single adhesive pad for retaining the respective applicator and grounding electrodes.

FIG. 4 discloses a separate casing having dual connecting wires 13 to a single, applicator-grounding electrode pad 18. As with other electrodes, the connecting wires could be attached at quick-release clips mounted on the back face of the electrodes. A primary advantage of this embodiment is the restricted conducted path which limits current flow to the area generally between the electrode surfaces. As with Example II, the single applicator/electrode pad could be trimmed to fit conveniently around awkward body contours.

To facilitate easy identification of the treated area, a non-ionic form of dye may be impregnated in the adhesive substance, such that upon removal of the electrode pad a color marking remains on the treated tissue. Without having observed the iontophoresis treatment, a subsequent attending physician or nurse could make the appropriate injection, surgery or other treatment required without guessing as to the actual location of the previously treated area. The dye can be permanent, semi-permanent or temporary depending upon the future needs for treatment area identification. Where only temporary marking is required, an impression ridge 19, FIG. 5 will leave a slighly reddened line circumscribing the treated region. If an impression ridge is used, it is important to ensure that skin in the conduction path is not tensed since this will decrease the local resistance and increase current flow in an non-uniform manner. For this reason the dotted line in FIG. 5A represents the perimeter of the conduction path, current flow being thereby isolated from tissue tensed by the impression ridge. It will be apparent that other means for marking the area of treatment are possible and may be necessary depending on the color and nature of the tissue to be treated.

We claim:

1. An iontophoresis device for epidermal application, comprising:
   a. a constant current source;
   b. applicator and grounding electrodes for emplacement upon patient tissue to provide a current path therethrough for performing iontophoresis upon a portion of said tissue;
   c. means for electrically connecting said current source to said electrodes to thereby produce a voltage differential across said electrodes;
   d. an impedance checking circuit coupled to said electrodes and having means for setting predetermined limits of impedance as measured across said electrodes which mark the bounds of safe operation for said device, said impedance checking circuit also having means to signal the occurrence of impedance values outside these predetermined limits;
   e. a safety-shutdown circuit coupled to said impedance checking circuit and having means responsive to said impedance value signal for preventing current flow and voltage differential across said electrodes.

2. An iontophoresis device as defined in claim 1, wherein said means for setting predetermined limits of impedance includes means to preset a predetermined upper limit as the maximum impedance at which the device will operate.

3. An iontophoresis device as defined in claim 1, wherein said means for setting predetermined limits of impedance includes means to preset a predetermined upper limit and predetermined lower limit as the operable range for the device.

4. An iontophoresis device as defined in claim 1, wherein said impedance checking circuit utilizes a comparator component to monitor said impedance.

5. An iontophoresis device as defined in claim 1, wherein said safety-shutdown circuit utilizes an SCR triggering mechanism for de-energizing the current source.

6. An iontophoresis device as defined in claim 1, comprising the additional element of an automatic timing means coupled to said current source and operable to preset the duration of iontophoresis treatment.

7. An iontophoresis device as defined in claim 1, further comprising a damping circuit coupled to said current source and operable to preclude sudden variations in current flow and voltage change.

8. An iontophoresis device as defined in claim 1, wherein said electrodes include a source of ionic medicament for conduction into patient tissue upon application of said current.

9. An iontophoresis device as defined in claim 8, wherein said medicament is selected from the group of materials consisting of ionic anesthetizing agents and ionic sterilizing agents.

* * * * *